United States Patent [19]

Alderman et al.

[11] Patent Number: 4,816,298

[45] Date of Patent: Mar. 28, 1989

[54] METHOD OF MAKING A GRANULAR, COLD WATER DISPERSIBLE COATING COMPOSITION

[75] Inventors: Daniel A. Alderman; Gary J. Schulz, both of Midland, Mich.

[73] Assignee: The Dow Chemical Company, Midland, Mich.

[21] Appl. No.: 125,956

[22] Filed: Nov. 27, 1987

[51] Int. Cl.$^4$ ............................ B05D 3/08; B05D 1/02
[52] U.S. Cl. ................................ 427/212; 106/126; 106/189; 106/213
[58] Field of Search ............... 106/189, 213, 126; 427/421, 212

[56] References Cited

U.S. PATENT DOCUMENTS

| | | | |
|---|---|---|---|
| 3,117,014 | 1/1964 | Klug | 106/213 |
| 3,314,809 | 4/1967 | Klug | 106/197.1 |
| 4,543,370 | 9/1985 | Porter et al. | 523/100 |

OTHER PUBLICATIONS

R. W. Hicks, J. R. Morton, and J. G. Fenic, "How to Design Agitators for Desired Process Response", *Chemical Engineering*, Apr. 26, 1976, pp. 102–110.

*Primary Examiner*—Theodore Morris

[57] ABSTRACT

A method of making a cold water dispersible granular composition comprising a plasticizer and thermally moldable polymer, for example hydroxypropyl methylcellulose, hydroxypropyl cellulose, carboxymethylcellulose, or hydroxy ethylcellulose. The method comprises, extruding the composition at elevated temperatures to form an extruded material and grinding the extruded material to form a granular product. The granules are very dispersible in cold water and when added to cold water, the solution can be used in coating operations, such as to coat pharmaceuticals, foods and food supplements to protect, color, harden, make foods more palatable or mask the taste of solid dosage forms.

18 Claims, No Drawings

METHOD OF MAKING A GRANULAR, COLD WATER DISPERSIBLE COATING COMPOSITION

BACKGROUND OF THE INVENTION

This invention relates to a water-dispersible composition for coating articles with a polymer film.

It is highly desirable to provide a polymer film coating composition that is cold water dispersible. Those wishing to formulate pharmaceutical tablet coatings must either purchase each of the individual components and make their own formulation, or purchase a relatively dispersible coating composition which includes all or most of the ingredients in the tablet formulation. Putting a coating formulation together necessitates multiple weighings of ingredients and blending of same. Preparation of the coating requires dispersing the polymer into hot water with sufficient time required for cooling and hydration, or dispersing the polymer into room temperature water while under high shear conditions. In this latter method, additional time is required for the foam from shearing to subside. Otherwise, the polymer agglomerates, resulting in a dispersion which is not uniform and is therefore undesirable.

A dispersible powder coating disclosed in, Porter et al., U.S. Pat. No. 4,543,370, comprises hydroxypropyl methylcellulose, plasticizer, surfactant and optional pigments. When these ingredients are premixed dry and then added to room temperature water, due to the presence of the surfactant, the mixture's viscosity decreases. The formulated coating mixture disperses in water at room temperature and is usable about an hour after mixing.

A quantitative measurement of dispersibility in water can be generated by measuring the amount of agitation required to completely disperse the powders into water. The measure of agitation required for dispersion oan be rated on a scale of 0-10, 0 being minimal and 10 being violent agitation (see examples for test standards). Also, hydration time can be measured by a Brabender amylograph. Hydration is the time to achieve 90 percent of ultimate viscosity at a standard agitation level.

By measuring dispersibility and hydration, a dry powder mixture in room temperature water comprising hydroxypropyl methylcellulose, plasticizer and surfactant, which disperses at an agitation level of about 7 with a hydration time of 20 minutes. When pigments are added as taught in Porter et al, U.S. Pat. No. 4,543,370, allowing for better dispersibility, the agitation level drops to about 5 with a hydration time of less than 20 minutes.

It is known in the art to use dry powder mixtures in room temperature water as taught in U.S. Pat. No. 4,543,370, but these powder mixtures only have acceptable dispersion and hydration time in room temperature water. Thus, it would be highly desirable to formulate a cold water dispersible coating composition that is granular, with improved dispersibility and hydration time.

SUMMARY OF THE INVENTION

The invention is a method of making a cold water dispersible granular composition comprising a plasticizer and thermally moldable polymer, which can ce used as film coating. The method comprises:

(a) extruding a composition comprising a thermally moldable polymer and a pharmaceutical acceptable plasticizer at elevated temperatures to form an extruded material and (b) comminuting the resulting extruded material to form a granulated product.

A preferred embodiment includes solidifying the extruded matter by cooling the resulting matter to facilitate comminuting.

Generally, the solution granulated product can be added to cold water and is used in coating operations. The granular thermoplastic composition may be used to coat pharmaceuticals, foods and food supplements to protect, color, harden, make foods more palatable, or mask the taste of solid dosage forms.

The granular composition of the present invention dissolves more quickly in cold water than the dry powder blends of the prior art. Therefore, the composition is easier and less costly to use. Also, because of the granular characteristics, the flow of the composition is benefited and the hazards of dust explosions associated with powder compositions are reduced.

DETAILED DESCRIPTION OF THE INVENTION

This invention is a method of making a cold water dispersible granular composition comprising a plasticizer and a thermally moldable polymer, by thermal extrusion to form a composition which can be used as a film coating formulation.

By "thermally moldable polymer" is meant that the polymer, when in a suitable solvent, will mold or flow upon application of heat. Such polymers have thermally moldable temperatures which may be modified by adding more polymer, or less solvent, either of which would decrease the temperature needed to reach the thermally moldable temperature. Preferably, the polymer is pharmaceutically acceptable. The thermally moldable polymers include hydroxypropyl methyl-cellulose, hydroxypropyl cellulose, carboxymethylcellulose, or hydroxyethylcellulose.

At elevated temperatures and under high shear extrusion, the polymer dissolves in the plasticizer to form a thermoplastic composition. The plasticizers include propylene glycol, polyethylene glycol, or water.

By conventional means, the plasticizer and thermally gelable polymer are mixed to form a homogeneous blend. This can be done at the inlet of an extruder or in an external mixing device. Preferably, the blend is premixed and is slowly added to the extruder that has been heated by steam or other conventional means of heating. Other means of heating the blend could include preheating the blend before extrusion, heating the individual components of the blend before mixing or using the heat generated during manipulation of the polymer in the extruder to heat the material.

The material in the extruder is heated to or maintained at a temperature in the range from about 70° to about 150° C., preferably about 90° to about 110° C. The optimum temperature for extrusion will vary somewhat dependent upon the polymer, plasticizer and other factors, but the optimum temperature can readily be determined empirically. The temperature of the polymer may vary depending upon where it is in the extruder, but generally a uniform temperature profile is preferred. The temperature referred to herein is the polymer temperature in the extruder just before it passes through the die. High temperatures which can cause decomposition should be avoided. The heated blend forms a thermoplastic composition, thus allowing extrusion of the composition. The extruded material is a firm material appearing uniform in texture and color. Dependent upon the type of extruder used, the extruded material might be recycled until the strands are firm and uniform in texture.

The thermoplastic composition is extruded through a die, preferably a multiholed die, of any shape, size or design that is operable. After the extruded material is of the desired texture, it is air cooled to harden and reduce stickiness. Although cooling improves the ease of subsequent milling, the extruded material is hard enough at extrusion temperatures to chop and mill without air cooling. The strands are chopped by conventional means or in some embodiments may be sufficiently brittle so they will break on their own into short lengths forming pellets or flakes.

The pellets are ground in a mill to approximately 20 to 140 U.S mesh granules, although another means of achieving these granules is to use a die face cutter. It is also possible to minimize the degree of grinding by using a die that gives very thin extrusions suoh as about 0.012 inch thick sheets or about 0.04 inch diameter strands.

Pigments and surfactants may be added to the granules, or could be added to the blend before extrusion. Pigment dispersions typically used in pharmaceutical formulations, suoh as aluminum-lake pigments, colorants, such as dyes and the like, could be added to the blend. Surfactants, such as dioctylsodium sulfosuccinates or sodium lauryl sulphate, may optionally be added before or after the extrusion or milling to reduce surface tension of water in contact with the granules and increase wetting of the particles.

Typically, the thermoplastic composition to be extruded is from about 50 to about 95 weight percent cellulose ether polymer, from about 5 to about 50 weight percent plasticizer. The addition of pigments and surfactants are optional. Typically, the composition comprises from about 0 to about 0.3 weight percent surfactant. A pigment to polymer ratio from about 0:1 to about 3:1 by weight is operable. The addition of pigments may alter the typical composition and will provide better dispersibility. Preferably, with the addition of surfactants and pigments, the composition comprises from about 60 to about 90 weight percent cellulose ether polymer and pigment, from about 10 to about 40 weight percent plasticizer, from about 0 to about 0.3 weight percent of surfactant and from about 0 to about 1/1 pigment to polymer ratio by weight.

As previously discussed, a quantitative measurement of dispersion and hydration time can be made. The thermoplastic granular composition is very dispersible in water. The granular composition in preferred embodiments has a dispersion of 2 to 3 with a hydration time of 1–5 minutes.

The thermoplastic granular composition can be added to cold water under agitation to form a concentration solution. The solution can be used in a coating operation, spraying the solution directly onto a tablet bed in a conventional coater. The composition may be used to coat pharmaceuticals, foods, food supplements to protect, color, harden, make more palatable, and mask the taste of solid dosage forms.

Because the moldable polymer and plasticizer form an extrudable thermoplastic composition, little or no segregation of components occurs. Thus, the thermoplastic composition has good flow and low dusting characteristics, which in turn creates stability in use.

EXAMPLES

How Agitation Level and Hydration Time are Determined

Dispersibility is a quantitative measurement of the compositions dispersion in water, that is generated by measuring the amount of agitation required to completely disperse the composition in water. To measure dispersion, the test apparatus used is a baffled agitated vessel with a variable speed agitator. The vessel is a 4-liter beaker (about 6.1 inch diameter × about 10 inches high). The agitator has two 6-blade turbines with 45° pitched, ½ inch wide blades with a 2.8 inch diameter. One turbine is located at 6.5 inches from the bottom and the other is 2 inches from the bottom. The vessel is also equipped with four ½-inch×5 inch baffles that are mounted on two metal rings so that they are held about a ⅛ inch from the wall and can be set into the bottom of the vessel. The liquid level is filled to 8 inches from the bottom.

Table I presents a scale of agitation levels which is correlated with bulk fluid velocity. This information is taken from "How to Design Agitators for Designed Process Response", *Chemical Engineering*, pages 102–110, April 26, 1976, which is incorporated by reference in its entirety. The revolutions per minute required in the test apparatus described hereinbefore to achieve the tabulated agitation level has been calculated and is included in Table I.

TABLE I

| Process Requirements Set Degree of Agitation for Blending and Motion | | |
| --- | --- | --- |
| Level of Agitation | Bulk Fluid Velocity ft/min | 1 Gallon RPM |
| 1 | 6 | 74 |
| 2 | 12 | 148 |
| 3 | 18 | 221 |
| 4 | 24 | 295 |
| 5 | 30 | 370 |
| 6 | 36 | 440 |
| 7 | 42 | 520 |
| 8 | 48 | 590 |
| 9 | 54 | 664 |
| 10 | 60 | 738 |

Agitation Levels 1 and 2 are characteristic of applications requiring minimum fluid velocities to achieve the process result. Agitation at level 2 will:
 (a) blend miscible fluids to uniformity if specific gravity differences are less than 0.1;
 (b) blend miscible fluids to uniformity if the viscosity of the most viscous is less than 100 times that of the other;
 (c) establish complete fluid-batch control: and
 (d) produce a flat, but moving, fluid-batch surface.

Agitation levels 3 to 6 are characteristic of fluid velocities in most chemical process industries agitated batches. Agitation at level 6 will
 (a) blend miscible fluids to uniformity if specific gravity differences are less than 0.6:
 (b) blend miscible fluids to uniformity if the viscosity of the most viscous is less than 10,000 times that of the other:
 (c) suspend trace solids (>2 percent) with settling rates of 2 to 4 ft/min, and
 (d) produce surface rippling at lower viscosities.

Agitation levels 7 to 10 are characteristic of applications requiring high fluid velocity for the process result, such as in critical reactors. Agitation at level 10 will:
(a) blend miscible fluids to uniformity if specific gravity differences are less than 1.0;
(b) blend miscible fluids to uniformity if the viscosity of the most viscous is less than 100,000 times that of the other:
(c) suspend trace solids (<2 percent) with settling rates of 4 to 6 ft/min.; and
(d) provide surging surfaces at low viscosities.

The hydration time is measured by a Brabender amylograph, measuring the time to achieve 90 percent of ultimate viscosity at a standard agitation level of the Brabender amylograph, assuming that the mixture completely disperses in cold water prior to testing and is immediately tested thereof.

EXAMPLE 1

A. In a plastic bag, 4.5 lbs of polyethylene glycol 400 (polyglycol E400NF, sold by The Dow Chemical Company, Midland, Mich.) is added to 10.5 lbs hydroxypropyl methylcellulose. The components are mixed within the bag to form a blend which is 30 percent plasticizer.

B. Slowly add the blend to a Reitz RE-6 Extruder with a die plate having ⅛ inch diameter holes and a screw speed of 32 rpm. The jacket is heated with atmospheric steam. Recycle the extrudated material back into the extruder inlet several times until the temperature of the plasticized polymer is above 95° C., and the strands are firm and appear uniform in texture and color. The strands will break in their own into short lengths.

C. Cool the strands to room temperature.

D. Break the strands into short lengths to form pellets and grind them with a lab Wiley mill equipped with a 20 mesh screen to form a granular coating formulation that will disperse in cold water with mild agitation and dissolve in less than 5 minutes and has a dispersibility (level of agitation) of 2.

EXAMPLE 2

A. In a plastic bag, 6.0 lbs of polyethylene glycol 400 (polyglycol E400NF, sold by The Dow Chemical Company, Midland, Mich.) is added to hydroxypropyl methylcellulose. The components are mixed within the bag to form a blend which is 40 percent plasticizer.

B. Slowly add the blend to a Reitz RE-6 Extruder with a die plate having ⅛ inch diameter holes and a screw speed of 72 rpm. The jacket heated with atmospheric steam. Recycle the extruded material back into the extruder inlet several times until the temperature of the plasticized polymer is above 95° C., and the strands are firm and appear uniform in texture and color. The strands will break on their own into short lengths.

C. Cool the strands to room temperature.

D. Break the strands into short lengths to form pellets and grind them with a model 197 Quadro Comil equipped with a 20 mesh screen to form a granular coating formulation that will disperse in cold water with very mild agitation and dissolve in less than 1 minute and has a dispersibility of 2.

EXAMPLE 3

A. In a platic bag, 2.25 lbs of polyethylene glycol and 2.25 lbs of propylene glycol 400 (polyglycol E400NF, sold by The Dow Chemical Company, Midland, Mich.) are added to 10.5 lbs hydroxypropyl methylcellulose. The components are mixed within the bag to form a blend which is 30 percent plasticizer (15 percent polyethylene glycol and 15 percent propylene glycol).

B. Slowly add the blend to a Reitz RE-6 Extruder with a die plate having ⅛ inch diameter holes and a screw speed of 70 rpm. The jacket is heated with atmospheric steam. Recycle the extruded material back into the extruder inlet several times until the temperature of the plasticized polymer is above 92° C., and the strands are firm and appear uniform in texture and color.

C. Cool the strands to room temperature.

D. Break the strands into short lengths to form pellets and grind them with a lab Wiley mill equipped with a 20 mesh screen to form granular coating formulation that will disperse in cold water with very mild agitation and dissolve in less than 5 minutes and has a dispersibility of 2.

EXAMPLE 4

A. In a plastic bag, 3.0 lbs of polyethylene glycol and 3.0 lbs of propylene glycol 400 (polyglycol E400NF, sold by The Dow Chemical Company, Midland, Mich.) are added to 9.0 lbs of hydroxypropyl methylcellulose. The components are mixed within the bag to form a blend which is 40 percent plasticizer (20 percent polyethylene glycol and 20 percent propylene glycol).

B. Slowly add the blend to a Reitz RE-6 Extruder with a die plate having ⅛ inch diameter holes and a screw speed of 70 rpm. The jacket is heated with atmospheric steam. Recycle the extruded material back into the extruder inlet several times until the temperature of the plasticized polymer is above 82° C. and the strands are firm and appear uniform in texture and color. The strands will break on their own into short lengths.

C. Cool the strands to room temperature.

D. Break the strands into short lengths to form pellets and grind them with a model 197 Quadro Comil Mill equipped with a 20 mesh screen to form a granular coating formulation that will disperse in cold water with very mild agitation and dissolve in less than 5 minutes and has a dispersibility of 2.

What is claimed is:

1. A method of coating a tablet composition with a cold water dispersible granular composition comprising a plasticizer and a thermally moldable polymer, wherein the method comprises,
   (a) extruding a composition comprising a thermally moldable polymer and a plasticizer at an elevated temperature of at least 70° C. to form an extruded material;
   (b) comminuting the resulting extruded material to form a granular product;
   (c) mixing the granular product in cold water wherein the granular product disperses and hydrates quickly to form a concentrated solution; and
   (d) spraying the concentrated solution onto a tablet bed in conventional coating apparatus, wherein, an edible composition is coated.

2. The method in claim 1, wherein before comminuting, the extruded material is cooled to a form suitable for grinding.

3. The method in claim 1, wherein the temperature at whioh the composition is extruded is from about 70° to about 150° C.

4. The method in claim 1, wherein the temperature at which the composition is extruded is from about 90° to about 110° C.

5. The method in claim 1, wherein the thermally moldable polymer is a cellulose ether.

6. The method in claim 5, wherein the cellulose ether is selected from the group consisting of hydroxypropyl methylcellulose, hydroxypropyl cellulose, carboxymethylcellulose, hydroxyethylcellulose.

7. The method of claim 1, wherein the plasticizer is selected from the group consisting of propylene glycol, polyethylene glycol and water.

8. The method in claim 1, wherein the composition comprises about 50 to about 95 weight percent cellulose ether, and about 5 to about 50 weight percent plasticizer.

9. The method in claim 1, wherein the composition comprises about 60 to about 90 weight percent cellulose ether or pigment and about 10 to about 40 weight percent plasticizer.

10. The method of claim 1, wherein the pigment to cellulose ether ratio by weight is from about 0:1 to about 3:1.

11. The method of claim 1, wherein the composition also contains a colorant such as an aluminum-lake pigment or a dye.

12. A coated tablet composition made from the method of claim 1.

13. The product of claim 12 wherein the particle size of the granules is a mesh size from about 20 to about 140 U.S. Sieve Series.

14. The product in claim 12 comprising from about 50 to about 95 weight percent cellulose ether and from about 5 to about 50 weight percent plasticizer.

15. The product in claim 12 comprising from about 60 to about 90 weight percent cellulose ether and pigment and from about 10 to about 40 weight percent plasticizer and the pigment to cellulose ether ratio is in the range from about 0:1 to 3:1 by weight.

16. The product in claim 12 wherein the composition extruded at a temperature from about 70° to about 150° C.

17. The product in claim 12 wherein the composition has been extruded at a temperature from about 90° to about 110° C.

18. A method as in claim 1 wherein the edible composition is a pharmaceutical.

* * * * *

UNITED STATES PATENT AND TRADEMARK OFFICE
CERTIFICATE OF CORRECTION

PATENT NO. : 4,816,298

DATED : March 28, 1989

INVENTOR(S) : Daniel A. Alderman and Gary J. Schulz

It is certified that error appears in the above-identified patent and that said Letters Patent is hereby corrected as shown below:

Column 1, line 38, "oan" should read --can--
Column 1, line 65, "ce" should read --be--
Column 3, line 21, "scoh" should read --such--
Column 3, line 27, "scoh" should read --such--
Column 5, line 65, "platic" should read --plastic--
Claim 3, column 6, line 64, "whioh" should read --which--

Signed and Sealed this

Twenty-fourth Day of April, 1990

Attest:

HARRY F. MANBECK, JR.

*Attesting Officer*       *Commissioner of Patents and Trademarks*